(12) United States Patent
Horn et al.

(10) Patent No.: US 7,761,134 B2
(45) Date of Patent: Jul. 20, 2010

(54) SYSTEM AND METHOD FOR MODELING A TRACKING CURVE OF AN IN VIVO DEVICE

(75) Inventors: Eli Horn, Kiryat Motzkin (IL); Daniel Gat, Haifa (IL); Raphael Rabinovitz, Raanana (IL); Yaacov Nitzan, Herzeliya (IL)

(73) Assignee: Given Imaging Ltd., Yoqneam (IL)

( * ) Notice: Subject to any disclaimer, the term of this patent is extended or adjusted under 35 U.S.C. 154(b) by 822 days.

(21) Appl. No.: 11/583,852

(22) Filed: Oct. 20, 2006

(65) Prior Publication Data
US 2008/0147087 A1 Jun. 19, 2008

(51) Int. Cl.
*A61B 5/00* (2006.01)
*A61B 1/00* (2006.01)

(52) U.S. Cl. ........................ 600/424; 600/117; 600/118; 600/476

(58) Field of Classification Search ................. 600/416, 600/407, 104–107, 117, 109, 476, 424; 348/76, 348/4; 434/267
See application file for complete search history.

(56) References Cited

U.S. PATENT DOCUMENTS

| | | | |
|---|---|---|---|
| 4,219,821 A | 8/1980 | Selim | |
| 4,278,077 A | 7/1981 | Mizumoto | |
| 4,329,881 A | 5/1982 | Schloss | |
| 4,936,823 A | 6/1990 | Colvin et al. | |
| 4,939,646 A * | 7/1990 | Essinger et al. | 382/128 |
| 5,042,486 A | 8/1991 | Pfeiler et al. | |
| 5,211,165 A | 5/1993 | Dumoulin et al. | |
| 5,279,607 A | 1/1994 | Schentag et al. | |
| 5,429,132 A | 7/1995 | Guy et al. | |
| 5,515,853 A | 5/1996 | Smith et al. | |
| 5,592,180 A | 1/1997 | Yokev et al. | |
| 5,604,531 A * | 2/1997 | Iddan et al. | 348/76 |
| 5,697,377 A | 12/1997 | Wittkampf | |
| 5,697,384 A | 12/1997 | Miyawaki et al. | |
| 5,736,958 A | 4/1998 | Turpin | |
| 5,913,820 A | 6/1999 | Bladen et al. | |

(Continued)

FOREIGN PATENT DOCUMENTS

EP 0 667 115 8/1995

(Continued)

OTHER PUBLICATIONS

U.S. Appl. No. 09/800,469, filed Mar. 8, 2001, Meron et al.

(Continued)

*Primary Examiner*—Eric F Winakur
*Assistant Examiner*—Lawrence N Laryea
(74) *Attorney, Agent, or Firm*—Pearl Cohen Zedek Latzer, LLP (57) ABSTRACT

A system and method to model a tracking curve of an in-vivo device capturing in-vivo data of the colon is provided. Data analysis is performed on a raw tracking curve to identify one or more milestone data points that correspond to defined locations in the colon. A modeled path may be defined between and along the selected milestone data points. Raw tracking curve data may be translated to modeled data along the modeled path. The modeled tracking curve may be displayed alongside a streaming display of captured in-vivo image frames of the colon.

12 Claims, 7 Drawing Sheets

U.S. PATENT DOCUMENTS

| | | | |
|---|---|---|---|
| 5,993,378 | A | 11/1999 | Lemelson |
| 6,172,640 | B1 | 1/2001 | Durst et al. |
| 6,188,355 | B1 | 2/2001 | Gilboa |
| 6,190,395 | B1 | 2/2001 | Williams |
| 6,233,476 | B1 | 5/2001 | Strommer et al. |
| 6,240,312 | B1 | 5/2001 | Alfano et al. |
| 6,453,190 | B1 | 9/2002 | Acker et al. |
| 6,580,938 | B1 | 6/2003 | Acker |
| 6,690,963 | B2 | 2/2004 | Ben-Haim et al. |
| 6,718,193 | B2 * | 4/2004 | Knoplioch et al. .......... 600/407 |
| 6,857,878 | B1 * | 2/2005 | Chosack et al. ............. 434/267 |
| 6,904,308 | B2 | 6/2005 | Frisch et al. |
| 6,934,573 | B1 | 8/2005 | Glukhovsky et al. |
| 7,009,634 | B2 | 3/2006 | Iddan et al. |
| 2002/0103417 | A1 | 8/2002 | Gazdzinski |
| 2003/0013370 | A1 | 1/2003 | Glukhovsky |
| 2003/0167000 | A1 | 9/2003 | Mullick et al. |
| 2003/0208107 | A1 | 11/2003 | Refael |
| 2004/0225223 | A1 | 11/2004 | Honda et al. |
| 2005/0048456 | A1 * | 3/2005 | Chefd'hotel et al. ........ 434/267 |
| 2005/0148816 | A1 | 7/2005 | Frisch et al. |
| 2006/0069317 | A1 | 3/2006 | Horn et al. |

FOREIGN PATENT DOCUMENTS

| | | |
|---|---|---|
| EP | 1260176 | 11/2002 |
| EP | 1 676 522 | 7/2006 |
| IL | 175930 | 5/2001 |
| IL | 143260 | 9/2006 |
| JP | 5745833 | 3/1982 |
| JP | 4109927 | 10/1992 |
| JP | 6154191 | 6/1994 |
| JP | 6285044 | 10/1994 |
| JP | 711985 | 5/1995 |
| JP | 7255692 | 10/1995 |
| JP | 2001046358 | 2/2001 |
| JP | 2001231186 | 8/2001 |
| JP | 2001231187 | 8/2001 |
| JP | 2006-138725 | 5/2002 |
| JP | 2003-19111 | 1/2003 |
| WO | WO 98/11816 | 3/1998 |
| WO | WO 99/32028 | 7/1999 |
| WO | WO 00/10456 | 3/2000 |
| WO | WO 01/06917 | 2/2001 |
| WO | WO 01/08548 | 2/2001 |
| WO | PCT/IL01/00217 | 3/2001 |
| WO | WO 03/021529 | 3/2003 |
| WO | WO 03/028224 | 4/2003 |
| WO | WO 2004/036803 | 4/2004 |
| WO | WO 2005/062717 | 7/2005 |
| WO | WO 2006/003652 | 1/2006 |

OTHER PUBLICATIONS

U.S. Appl. No. 09/881,810, filed Jun. 18, 2001, Meron et al.
"Localization of a wireless capsule endoscope in the GI Tract", Gastrointestinal Endoscopy 2001;53:AB126.
Nam, et al., "A method for Position Detection of the wireless capsule endoscopes Module Using the Solution of Nonlinear Simultaneous Equations", Sensors Conference 2002, p. 377.
Nam, et al., "A method for Position Detection of Miniaturized Telemetry Module Using the Solution of Nonlinear Simultaneous Equations", 2002.
Office Action mailed May 18, 2004 U.S. Appl. No. 10/150,018.
Office Action mailed Mar. 31, 2006 Application No. 02010270.3.
Office Action mailed Jul. 25, 2006 Application No. 02010270.3.
Office Action mailed Jun. 29, 2006 Application No. 02010270.3.
Park, et al., "A Technique for Position Detection of Miniatured Wireless Telemetry Module in the Human Body", Proceedings of the $32^{nd}$ ISR (International Symposium on Robotics), Apr. 19-21, 2001, pp. 1888-1892.
Park, et al., "Design of Bi-directional and Multi-Channel Miniaturized Telemetry Module for Wireless Endoscopy", $2^{nd}$ Annual International IEEE-EMBS Special Topic Conference on Microtechnologies in Medicine &Biology, May 2-4, 2002, Madison, Wisconsin USA pp. 273-276.
Park, et al., "Design of Miniaturized Telemetry Module for Bi-Directional Wireless Endoscopy", May 2-4, 2002.
Park, et al., "A Technique for Localization of Biomedical Telemetry Sensor in Human Body", Proceedings of the International Sensor Conference 2001, Seoul, Korea.
www.ibcdigital.com/ibc/animation_galleries/visualization.
European Search Report for European Patent Application No. EP07118957.5, Apr. 11, 2008.

* cited by examiner

SYSTEM AND METHOD FOR MODELING A TRACKING CURVE OF AN IN VIVO DEVICE

FIELD OF THE INVENTION

The present invention relates to the field of tracking in-vivo sensing devices, and more particularly to modeling a tracking curve of an in-vivo sensing device through the colon.

BACKGROUND OF THE INVENTION

In vivo imaging systems may be used, for example, to diagnosis pathology. If pathology is detected, for example by inspecting an image stream captured by the in-vivo device, a physician may want to establish the location along the gastrointestinal (GI) tract where the pathology was detected. The location of the pathology may give the physician valuable information regarding the accessibility of the location for treatment and/or the nature of the pathology.

Some in-vivo systems for imaging the GI tract, e.g. swallowable video capsule systems, may include a tracking system to locate the position of the in-vivo sensing device in space over time. When tracking the location of an in-vivo device traveling along the colon, it may be difficult to correlate the position in space of the in-vivo sensing device over time with a position and/or advancement of the in-vivo device along the GI tract. Typically, tracking data may be noisy and conventional filtering not be enough to improve the quality of the data.

In addition, the position of the colon may change over time as it may be flexible. An autonomous swallowable video capsule may have dimensions that are smaller than a lumen diameter of the colon and the video capsule may toss and tumble as it passes through the colon. Capsule movement through the colon tracked by the tracking system may appear erratic. The capsule may stagnate, in some sections of the colon, may pass quickly over other sections, and may retract for a distance. As such it may be difficult for a physician to decipher from the tracking curve of the location of the in-vivo device in space, how far along or in what section of the colon a point of interest, e.g. pathology may have been detected.

SUMMARY OF THE INVENTION

Some embodiments of the invention may include, for example, a model based tracking system and method to display noisy tracking data of the location of an in-vivo device through a colon.

Some embodiments of the present invention may include a method or a system for modeling a raw tracking curve of an in-vivo device passing through a colon by, for example, identifying milestone data points on the raw tracking curve corresponding to defined locations in the colon, defining a modeled path between the milestone data points on the raw tracking curve, and translating at least a portion of the raw tracking curve to modeled tracking curve along the modeled path. Milestone data points may include for example, flexure points, specific sections of the colon such as the ceacum, transverse colon, rectum and/or small intestine. Other points may be included in milestone data points.

Other embodiments may include determining signal strengths of received signals, e.g. image signals, where the received signals correspond to data points on the raw tracking curve and identifying the milestone data points based on the signal strengths of the received signals.

According to other embodiments of the present invention, image data captured in-vivo may be received and image data analysis may be performed, e.g. by a colon section detector unit, to identify one or more milestone data points on the raw tracking curve. In other examples, identification of one or more milestone data points may be user assisted and user input to identify at least one milestone data point may be received.

According to yet other embodiments of the present invention a system and method may include displaying a streaming display of image frames captured by the in-vivo device and displaying a moving marker along the modeled path to indicate a modeled location of the in-vivo device corresponding to a currently displayed image frame from the streaming display of the image frames.

Some embodiments may include, for example, a colon section detector unit, to detect the passage of an in vivo device through a section of the colon.

Some embodiments may include, for example, a colon section detector unit to detect the passage of an in-vivo device through a flexure point.

Some embodiments may include, for example, a system to display a model based tracking curve of the advancement of the in-vivo device through a colon.

BRIEF DESCRIPTION OF THE DRAWINGS

The subject matter regarded as the invention is particularly pointed out and distinctly claimed in the concluding portion of the specification. The invention, however, both as to organization and method of operation, together with containers, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, components and circuits have not been described in detail so as not to obscure the present invention.

Although a portion of the discussion may relate to in-vivo imaging devices, systems, and methods, the present invention is not limited in this regard, and embodiments of the present invention may be used in conjunction with various other in-vivo sensing devices, systems, and methods. For example, some embodiments of the invention may be used, for example, in conjunction with in-vivo sensing of pH, in-vivo sensing of temperature, in-vivo sensing of pressure, in-vivo sensing of electrical impedance, in-vivo detection of a substance or a material, in-vivo detection of a medical condition or a pathology, in-vivo acquisition or analysis of data, and/or various other in-vivo sensing devices, systems, and methods.

Some embodiments of the present invention are directed to a typically one time use or partially single use detection and/or analysis device. Some embodiments are directed to a typically swallowable in-vivo device that may passively or actively progress through a body lumen, e.g., the gastrointestinal (GI) tract, for example, pushed along by natural peristalsis. The in-vivo device may be, for example, a sensing device, an imaging device, a diagnostic device, a detection device, an analysis device, a therapeutic device, or a combination thereof. In some embodiments, the in-vivo device may include an image sensor or an imager. Other sensors may be included, for example, a pH sensor, a temperature sensor, a pressure sensor, sensors of other in-vivo parameters, sensors of various in-vivo substances or compounds, or the like.

Devices, systems and methods according to some embodiments of the present invention, including for example in-vivo sensing devices, receiving systems and/or display systems, may be similar to embodiments described in U.S. Pat. No. 5,604,531 to Iddan et al., entitled "In-vivo Video Camera System", and/or in U.S. Pat. No. 7,009,634, entitled "Device for In-Vivo Imaging", issued on Mar. 7, 2006, and/or in U.S. Pat. No. 6,904,308 to Frisch et al., entitled "Array System and Method for Locating and In Vivo Signal Source", all of which are hereby incorporated by reference in their entirety. Devices and systems as described herein may have other configurations and/or sets of components. For example, an external receiver/recorder unit, a processor and a monitor, e.g., in a workstation, such as those described in one or more of the above publications, may be suitable for use with some embodiments of the present invention. Some embodiments of the present invention, for example, may be practiced using an endoscope, a needle, a stent, a catheter, or other suitable devices.

Figure 1:
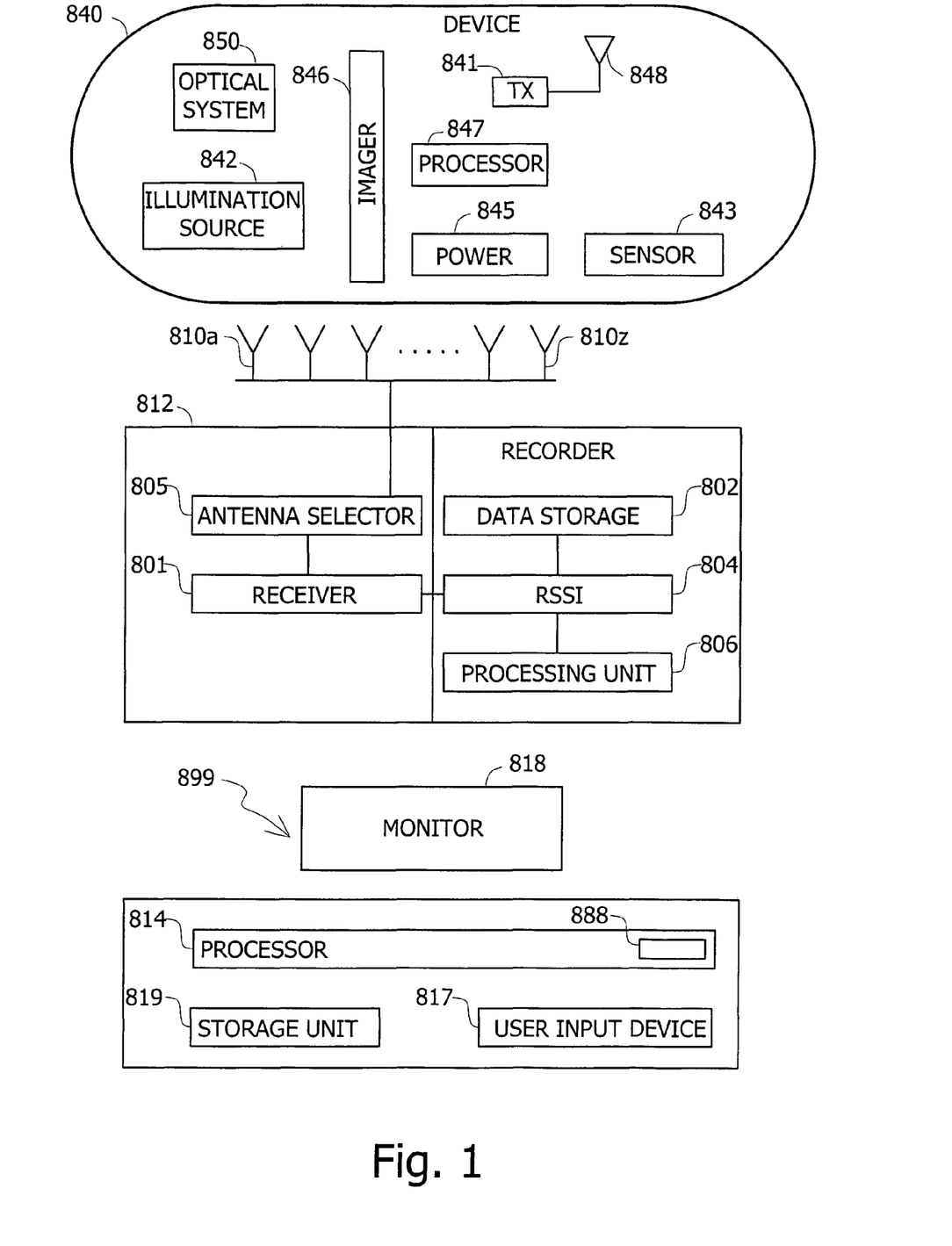
FIG. 1 is a schematic block diagram of an in-vivo imaging system including model based tracking to track the location of an in-vivo imaging device through a colon in accordance with some embodiments of the invention.

FIG. 1 schematically illustrates an in-vivo sensing system in accordance with an embodiment of the present invention. In some embodiments, the system may include, for example, an in-vivo imaging device 840 having an imager 846, an illumination source 842, a power source 845, and a transmitter 841. In some embodiments, device 840 may be implemented using a swallowable capsule, but other type of devices or suitable implementations may be used. Outside a patient's body may be, for example, an image data recorder 812 including or operatively connected to, for example, an antenna, an antenna belt, or an antenna array 810, one or more storage units 802 and/or 819, one or more processors 806 and 814, a user input device(s) 817 and a monitor 818. In one embodiment, for example, the storage unit 819, data processor 814, user input device(s) 817 and/or the monitor 818 may optionally be implemented as a workstation 899 which may include, for example, a multi-purpose or dedicated computer or computing platform. According to embodiments of the present invention, workstation data processor 814 may include a colon section detector unit 888. Colon section detector unit 888 may be, for example, a dedicated processor, may be implemented in software, or may be implemented in another manner. In other examples, the colon section detector unit 888 may be included in full or in part in the recorder processor 806.

According to embodiments of the present invention, colon section detector unit 888 may detect and/or identify at least one milestone data point on raw tracking data for example including or corresponding to a defined location in the colon and to translate the raw tracking curve to a modeled curve. In addition, colon section detector unit 888 may construct a model based tracking curve to be displayed for example on monitor 818. In other examples colon section detector unit 888 may detect and/or identify raw tracking data and/or image data and/or a stream of raw tracking data and/or image data corresponding to a specific section in the colon and may mark that data as data captured from the specific section of the colon. Other data besides raw tracking data and image data may be detected and/or identified. User input data may also be used and/or implemented, for example in addition to automatic detection by colon section detector 888, for detection and/or identification of data corresponding to specific section of the colon. In other examples, a similar device, system and method may be used to detect other section of the GI tract in addition and/or instead of the colon.

Transmitter 841 may operate wirelessly, for example, by using radio frequency (RF) waves; but in some embodiments, such as those where device 840 is included within an endoscope, transmitter 841 may transmit data via, for example, wire, optical fiber and/or other suitable methods.

Device 840 typically may be or may include an autonomous swallowable capsule, but device 840 may have other shapes and need not be swallowable or autonomous. Embodiments of device 840 are typically autonomous, and are typically self-contained. For example, device 840 may be a capsule or other unit where all the components are substantially contained within a container or shell, and where device 840 does not require any wires or cables to, for example, receive power or transmit information.

Recorder 812 may include an antenna and/or antenna array 810 having multiple antenna elements 810a to 810z, an antenna selector 805, a receiver 801, the data storage unit 802, a received signal strength indicator (RSSI) unit 804, and the processor 806. Data storage unit may store the raw tracking curve data detected. In alternate embodiments the data recorder 812 may include other combinations of components, and the components described may be divided among other units. The RSSI unit 804 may measure the signal strength of signals received by the receiver 801 from each of the antenna elements 810a through 810z, and the processor 806 may perform calculations to correlate the received signal with an estimated location of the source of the signal, e.g. a signal transmitted by antenna 848. Processor 806 may have other functions and may not correlate the received signal with an estimated location of the source of the signal. The antenna selector 805 may open a signal path to a single antenna element from which the receiver 801 will receive a signal. The antenna selector 805 may be adjusted to scan through all or subset of antenna elements 810a through 810z. The scan rate and pattern may be adjusted to maximize signal to noise ratios for the received signals.

The antenna array may be fixed to a body and/or worn on a body, and two or more antenna elements from the antenna array 810 may receive a signal from an in vivo device 840, e.g. the in-vivo device antenna 848. The signal strength of a plurality of received signals may be measured and an estimated location of the signal source may be derived from the signal strength measurements, e.g. by using triangulation measurements. A raw tracking data curve, raw tracking data and/or a raw tracking data curve may be constructed based on and/or derived from the estimated location of the signal source over time. For example, a raw tracking curve may be constructed as described in U.S. Pat. No. 6,904,308 incorporated herein. Other methods of constructing a raw tracking curve, e.g. a tracking curve based on position sensors indicating a position of the in-vivo device in space, may be implemented. The signal strength of the signal received, e.g. the strongest signal received from the antenna array 810, corresponding to data points on the raw tracking curve may be determined and saved.

In some embodiments, device 840 may communicate with an external receiving and display system (e.g., through recorder 812) to provide display of data, control, and/or other functions. Other embodiments may have other configurations and capabilities. For example, components may be distributed over multiple sites or units, and control information may be received from an external source. According to embodiments of the present invention recorder 812 may receive image data captured in-vivo and the colon section detector unit 888 may analyze the image data received. In some examples, colon section detector unit 888 and/or its functionality may be partially or fully incorporated within the recorder 812.

In one embodiment, device 840 may include an in-vivo video camera, for example, imager 846, which may capture and transmit images of, for example, the GI tract, e.g. the colon, while device 840 passes through the GI lumen. Image data recorder 812 may receive image data, e.g. image frames captured within the colon.

In one embodiment, imager 846, in device 840 may be operationally connected to transmitter 841. Transmitter 841 may transmit images to, for example, image recorder 812, which may send the data to data processor 814 and/or to storage unit 819. Transmitter 841 may also include control capability, although control capability may be included in a separate component.

In some embodiments, imager 846 may acquire in-vivo images, for example, continuously, substantially continuously, or in a non-discrete manner, for example, not necessarily upon-demand, or not necessarily upon a triggering event or an external activation or external excitement; or in a periodic manner, an intermittent manner, or an otherwise non-continuous manner.

Transmitter 841 may transmit image data continuously, or substantially continuously, for example, not necessarily upon-demand, or not necessarily upon a triggering event or an external activation or external excitement; or in a periodic manner, an intermittent manner, or an otherwise non-continuous manner.

Device 840 may include one or more illumination sources 842. Illumination sources 842 may, for example, illuminate a body lumen or cavity being imaged and/or sensed. An optional optical system 850 may optionally be included in device 840 and may aid in focusing reflected light onto imager 846 and/or performing other light processing operations.

Data processor 814 may analyze the data received via recorder 812 from device 840, and may be in communication with storage unit 819, e.g., transferring frame data to and from storage unit 819. Data processor 814 may also provide the analyzed data to monitor 818, where a user (e.g., a physician) may view or otherwise use the data, including, for example, image data, sensing data, location data, motility data, or other information. For example, processor 814 may control display of the modeled raw tracking curve. In one embodiment, data processor 814 and/or 806 may be configured for real time processing and/or for post processing of data. In the case that control capability (e.g., delay, timing, etc) is external to device 840, a suitable external device (such as, for example, data processor 814 or image recorder 812) may transmit one or more control signals to device 840.

Monitor 818 may display one or more images or a stream of images captured and/or transmitted by device 840, e.g., images of the GI tract or of other imaged body lumen or cavity. In one embodiment, for example, both an image and its position or location, e.g. the raw tracking curve may be presented using monitor 818 and/or may be stored using storage unit 819. Other systems and methods of storing and/or displaying collected image data and/or other data may be used.

In some embodiments, in addition to and/or instead of revealing pathological or other conditions of the GI tract or other body lumens, an embodiment of the invention may provide information about the location of these conditions. Suitable tracking devices and methods are described herein, as well as in embodiments of the above-mentioned U.S. Pat. No. 5,604,531 and/or U.S. Pat. No. 6,904,308, entitled "Array System and Method for Locating an In-Vivo Signal Source", both of which assigned to the common assignee of the present invention and fully incorporated herein by reference. Other suitable location identification systems and methods may be used in accordance with embodiments of the present invention.

In some embodiments, device 840 may capture and/or acquire an image, for example, once every half second, and may transmit the image data to recorder 812. Recorder 812 may receive the image data transmitted. Other constant and/or variable capture rates and/or transmission rates may be used.

Optionally, device 840 may include one or more sensors 843, instead of or in addition to a sensor such as imager 846. Sensor 843 may, for example, sense, detect, determine and/or measure one or more values of properties or characteristics of the surrounding of device 840, for example concurrently with capturing image frames with imager 846. For example, sensor 843 may include a pH sensor, a temperature sensor, an electrical conductivity sensor, a pressure sensor, or any other suitable in-vivo sensor.

In accordance with some embodiments of the invention, raw tracking data and/or localization data may be determined using, for example, data collected by or transmitted by in-vivo device 840 separate from location data itself. For example, tracking data may be inherent in a signal such as a data signal sent by the in-vivo device 840, or may be in a beacon sent by the in-vivo device 840, while other and additional data such as sensing data (e.g., image data, pH data, etc.) may be sent separately from tracking data. In one embodiment, sensing data may be considered non-tracking data collected by the in-vivo device 840. In some embodiments, tracking data may be inherent in a data signal which primarily contains sensed data.

The monitor 818 may present, for example, image data, preferably in the form of still and/or moving pictures, and a model based tracking curve, to indicate where the in-vivo device 840 was situated within a body lumen during the time period the image data presented on the monitor 818 was collected. Data other than image data may be presented on monitor 818 and the model based tracking curve may indicate where the in-vivo device 840 was situated during the time period the data presented on the monitor 818 was collected.

While in some embodiments, information gathering, storage and processing may be performed by certain units, the system and method of the present invention may be practiced with alternate configurations. In some embodiments, the colon section detector unit 888 may be located in part or as a whole inside device 840 (e.g., a swallowable capsule) or, alternatively, on a portable device (e.g., recorder 812) which may be worn on the patient. Furthermore, the components gathering image information need not be contained in a capsule, but may be contained in any other vehicle suitable for traversing a lumen in a human body, such as an endoscope, a stent, a catheter, a needle, or other suitable devices.

Figure 2A:
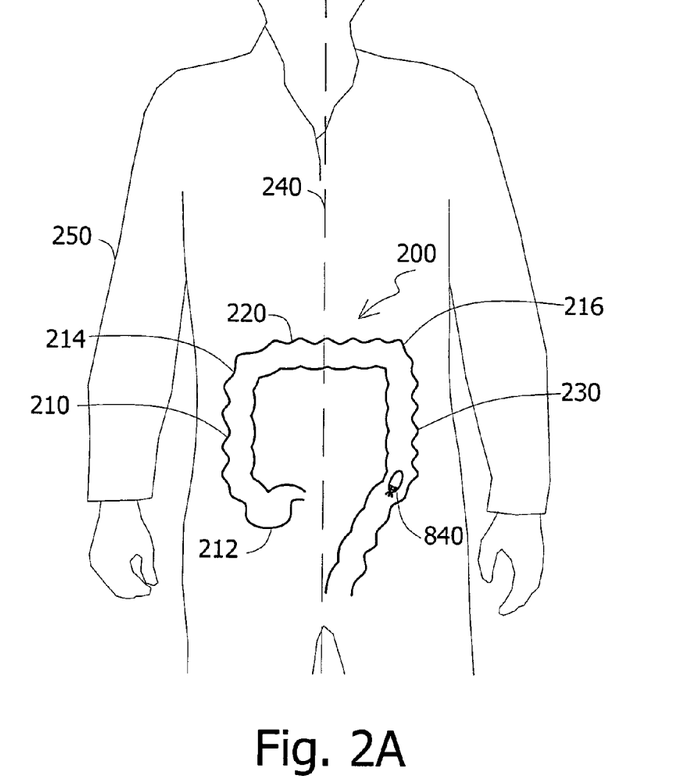
FIG. 2A is a schematic illustration of an in-vivo device advancing along a colon.

FIG. 2A is a schematic illustration of an in-vivo device 840 advancing along a colon 200 of a patient 250, in accordance with some embodiments of the invention. Typically the colon 200 may be schematically represented as having 'C' shape geometry such that the transverse section 220 of the colon may usually cross the mid-line axis 240 of the body 250 transporting its content from the right to the left side of the body. An in-vivo device 840 ingested through the mouth may enter the colon 200 through the ceacum 212, advance past the ascending colon 210, the transverse colon 220, and the descending colon 230 before existing the body through the rectum. The hepatic flexure 214 and the splenic flexure 216 may be transition points between the different sections of the colon 200. The transverse section of the colon 220 typically spans across the mid-line 240 of the body 250 and transports the in-vivo device 840 past the mid-line 240 of the body 250.

When in-vivo device 840 enters into the colon 200 it may reside/dwell in the ceacum 212 for a period of time, before advancing further. This may be due to the sac like structure of the ceacum 212. The in-vivo device 840 may remain in the ceacum 212, for example between a few minutes up to a few hours. In other examples, the in-vivo device may not stop at the ceacum at all. During the period while the in-vivo device 840 is present in the ceacum 212, the in-vivo device 840 may typically jitter, tumble, and/or move around in a volume of the ceacum 212, typically larger than the volume of the in-vivo device 840. Fluid flow and/or a contraction may initiate movement of the in-vivo device 840 along the ascending colon 210. It may typically take between about 10 minutes and about 5 hours for the in-vivo device 840 to pass the ascending colon past the hepatic flexure 214 and enter the transverse section of the colon 220. Other time periods are possible. For example, if the in-vivo device is actively propelled through the colon, the time periods may be shorter. In other examples, food and/or beverage intake may alter the time periods. Passage through the transverse section of the colon typically occurs over a short period of time, typically between 2 seconds and 30 minutes which advances the in-vivo device 840 past the splenic flexure 216 into the descending colon 230. Passage through the descending section of the colon 230, may be similar to the passage through the ascending section of the colon 210 and may occur over a period between about 10 minutes and about 5 hours.

Figure 2B:
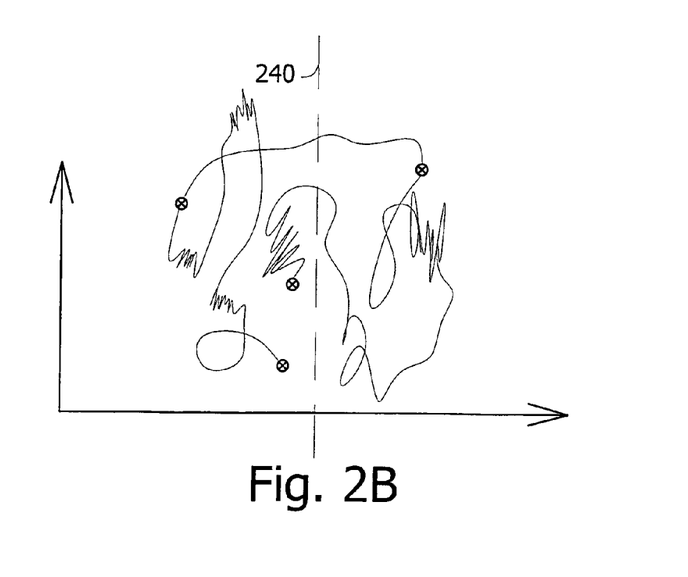
FIG. 2B is a schematic illustration of a sample tracking curve.

Reference is now made to FIG. 2B showing a raw data tracking curve of an in-vivo device traveling through a colon. The tracking curve shown may seem erratic and may not seem to follow an expected route through a 'C' shaped representation of the colon. The erratic behavior of the curve may be due to typical errors that may occur in tracking the location of the in-vivo device as well as for other reasons. For example, errors may occur when the signal source of the in-vivo device 840 changes its orientation with respect to the receiving antennas 810, such that the signal strength may be different. In other examples, the signal strength may attenuate at different rates over different types of tissues, causing errors in the tracking data. In other examples, errors may occur due to relative movement between the colon and the skin or between the receiving antennas 810 and the colon 200. In some examples, the typical shape of the colon may not resemble 'C' shaped geometry. In other examples, the colon may move in relation to the sensors typically positioned on the skin, e.g. due to body movements or due to contractions through the colon. Such movement may incur tracking errors. In addition, the secondary motion of the in-vivo device, e.g. tossing, turning, tumbling, and vibrating, may obscure the primary motion of the in-vivo device. In some embodiments, body movement sensors may used to measure the body movements so that for example they may later by removed from the tracking data information.

For all these reasons and other reasons it may be difficult for the physician to decipher or make use of the raw tracking curve obtained from sensing the position of the in-vivo device in space, e.g. the position relative to the receiving antennas. It may be difficult for a physician to determine at a point of time if the in-vivo device is in the ascending, transverse, and/or descending section of the colon or how far along the in-vivo device 840 has advanced through the colon 200. Automated analysis of the tracking curve by deciphering certain features of the curve and/or by introducing more information may enable translating the tracking curve to a model based curve having a predetermined path that models a simplified path through the colon 200 and thus providing the physician with a more useful locating and/or tracking tool. For example, a physician may obtain an indication of the location in the colon (or the section of the colon) where a specific data and/or image was acquired by the in-vivo device 840 and also on the rate of advancement of the in-vivo device 840 through the colon. This may give the physician indication of pathology, motility and/or motor function of specific section of the colon.

Figure 3:
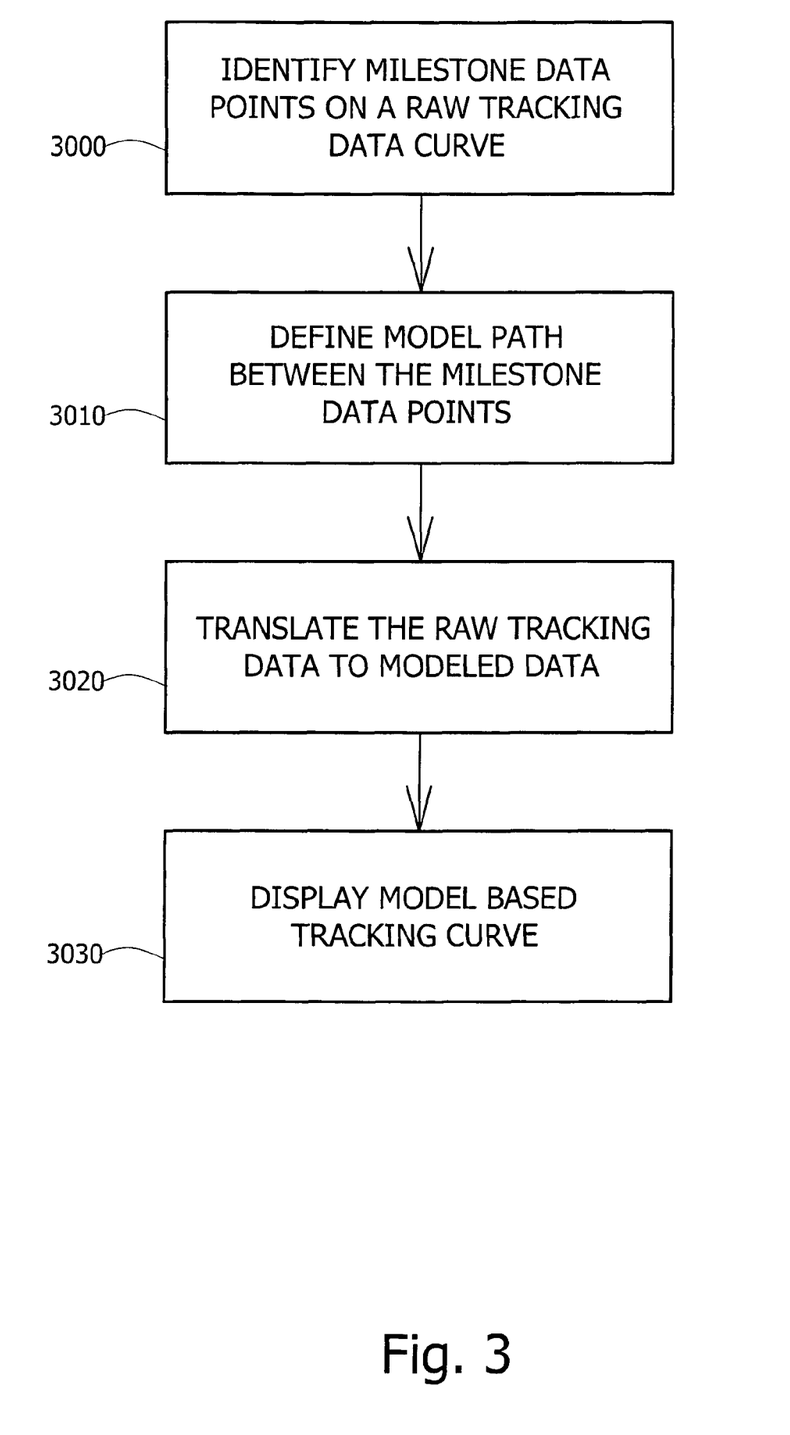
FIG. 3 is a flow chart describing a method for modeling raw tracking data curve according to embodiments of the present invention.

Reference is now made to FIG. 3 showing flow chart describing a method for modeling raw tracking data curve according to embodiments of the present invention. In block 3000 milestone data points on for example the raw tracking data curve that correspond to a defined location in the colon may be detected as may be described herein. In one example, detection of the milestone data points may be performed by colon section detector unit 888 based on analysis of the raw tracking data. In another example, detection of the milestone data points may be performed by colon section detector unit 888 based on image data captured in-vivo received by for example recorder 812, other data collected by in-vivo device 840, and/or based on a combination of data collected. In yet other examples detection of the milestone data may be performed at least partially by a user and/or heath professional. Sample milestone data points may include for example, data points corresponding to the ceacum, hepatic flexure, splenic flexure, and/or the rectum area. In other examples, sample milestone data may include a data point captured in the ascending colon, the transverse colon, and/or the descending colon. Other milestone data points may be detected and/or identified.

In block 3010 a modeled path between the detected milestone data points on the raw tracking curve may be modeled as may be described herein. In one example, the modeled path may be a straight line between two milestone data points. In other examples, the modeled path may be a defined curve between two or more defined milestone data points. Other modeled paths may be defined. In some embodiments, the milestone data points may be translated to a newly defined modeled position prior to defining the modeled path between the milestone data points.

In block 3020, raw tracking data and/or a portion of the raw tracking data, for example, raw tracking data, e.g. raw tracking data in the vicinity of the detected milestone data points and/or between the milestone data points may be translated to modeled tracking data points along the modeled path as may be described herein.

In block 3030 the modeled tracking curve may be displayed. In one example the tracking curve may be displayed together with a streaming display of the image data collected by the in-vivo device 840. For example, a marker may indicate to the user, viewer and/or health professional the location on the modeled base tracking curve corresponding to a displayed image frame captured by in-vivo device 840. In other example the display may not include a streaming display of the image frames. Other steps and methods may be implemented.

Figures 4A, 4B:
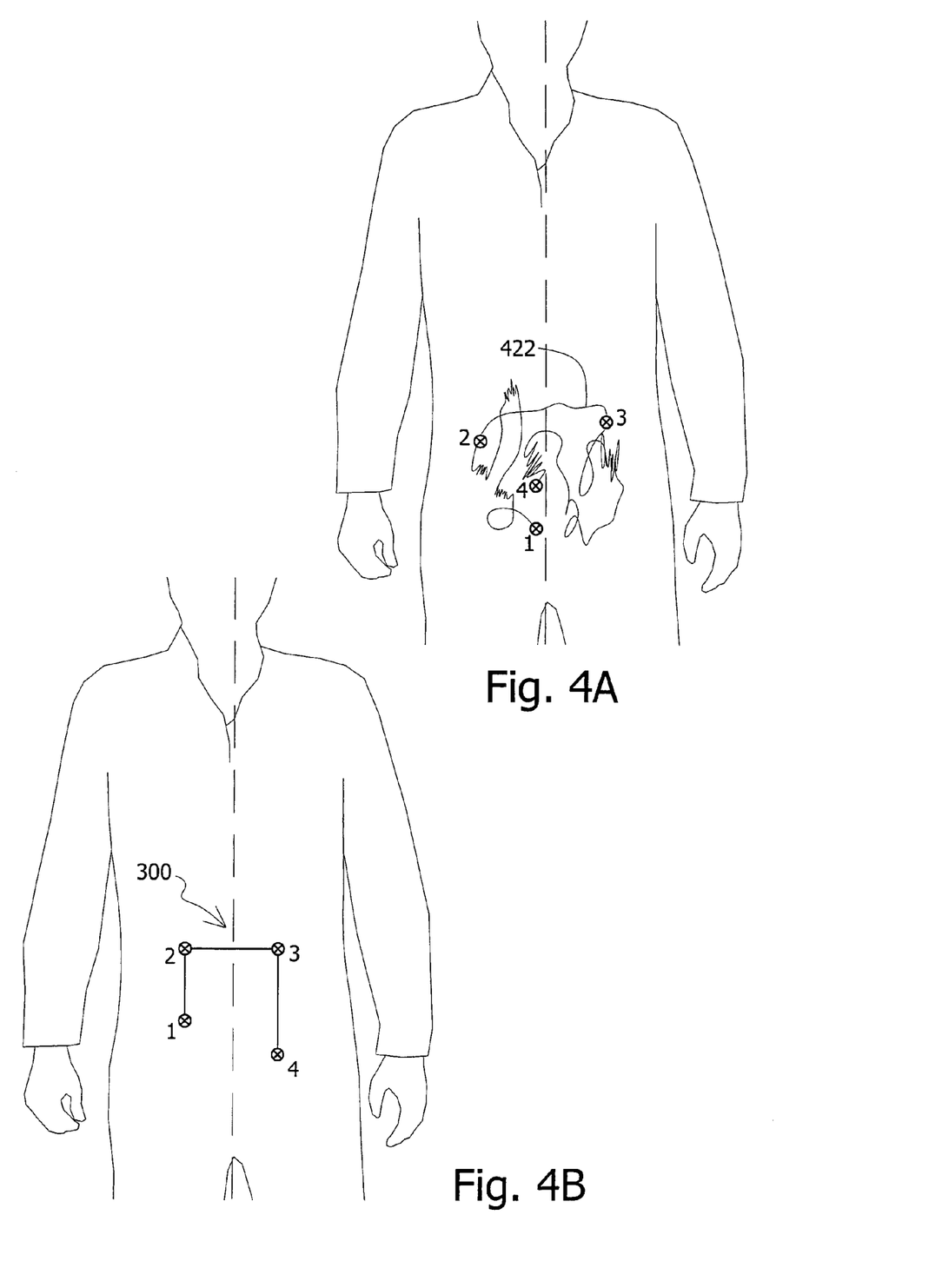
FIG. 4A is a schematic illustration of a sample tracking data curve with detected transition points in accordance with embodiments of the present invention.
FIG. 4B is a schematic illustration of a model based tracking curve constructed based on detected transition points in accordance with embodiments of the present invention.

Reference is now made to FIG. 4A showing schematic illustration of a sample tracking curve with detected transition points along the tracking curve in accordance with embodiments of the present invention and to FIG. 4B showing a schematic illustration of a model based tracking curve constructed based on the detected transition points in accordance with embodiments of the present invention. According to embodiments of the present invention, milestone data points on the raw tracking curve corresponding to the position of the in-vivo device 840 when situated in a defined location within colon, e.g. within a transition point in the colon such as the ceacum 212 marked as point '1', the hepatic flexure 214 marked as point '2', the splenic flexure 216 marked as point '3', and the rectum marked as point '4' may be identified by methods described herein. The hepatic flexure 214 marked as point '2', the splenic flexure 216 marked as point '3' may, for example mark the entrance and exit points of the transverse section of the colon 422 respectively. According to embodiments of the present invention, the path of the in-vivo device 840 between the tracking curve (FIG. 4A), to a modeled path following, for example, three straight lines forming a 'C' shaped path and/or curve (FIG. 4B). In other examples, the modeled path may have other pre-determined and/or modeled shape, e.g. 3 curved lines forming a curved 'C' shape and/or some other shape resembling a typical colon shape representation. In one example the position of the milestone data points, e.g. the transition points may be translated to modeled positions of the transition points to form the typical 'C' shaped of the colon. For example, the milestone data points may be translated to modeled milestone data points, e.g. points defining the shape of the desired modeled tracking curve. The modeled path may be displayed as a path connecting the modeled milestone data points. In other examples, the position of the transition points, e.g. the milestone data points in the raw tracking curve may be maintained during construction of the model tracking curve 300 and the modeled path may be defined and/or displayed as a path connecting the detected milestone data points.

In one example, the path between the ceacum marked as milestone datum point '1' and the hepatic flexure marked as milestone datum point '2' may be modeled as a first straight path, e.g. a path following a straight line. During the period in which the in-vivo device 840 travels within the ascending section of the colon, the in-vivo device 840 may tumble, change its orientation retract and move unpredictably. Changes in orientation and unsystematic advancement of in-vivo device 840 as well as movement of the colon 200 with respect to the location sensors, e.g. the antenna array 810 may make it difficult to decipher the advancement of the in-vivo device 840 through the ascending section of the colon as depicted in the raw tracking curve. Translating this apparently erratic movement to advancement along a modeled straight line may help give indication of the location and advancement of the in-vivo device 840 along the colon 200. FIG. 4B shows an example of a modeled first straight path of the ascending colon between milestone datum point '1' and milestone datum point '2'. Back and forth motion along the modeled straight path may be depicted by a marker sliding along the modeled path either backwards or forwards.

Typically passage through the transverse section of the colon occurs over a short period of time which advances the in-vivo device 840 past the splenic flexure 216 into the descending colon 230. In FIG. 4A the splenic flexure 216 on the raw tracking curve is marked as point '3'. Methods for detecting the splenic flexure 216 on the tracking curve may be as described herein. Due to the speed at which the in-vivo device 840 advances through the transverse colon, the tracking curve through the transverse colon 220 may be smoother than the tracking curve between other sections of the colon as may be demonstrated in FIG. 4A.

According to embodiments of the present invention, the path between the hepatic flexure milestone data point '2' and the splenic flexure milestone data point '3' may be modeled as a second straight line extending from the first straight line as may be shown in FIG. 4B as the line between milestone data point '2' and milestone data point '3'. Methods of modeling the path between the hepatic flexure milestone data point '2' and the splenic flexure milestone data point '3' may be similar to methods described for modeling the path between the ceacum milestone data point '1' and the hepatic flexure milestone data point '2'. Other suitable methods for modeling the path between the hepatic flexure milestone data point '2' and the splenic flexure milestone data point '3' may be used.

Passage through the descending section of the colon 230, may be similar to the passage through the ascending section of the colon 210. Passage through the descending section of the colon 230 may also be accompanied by erratic motion of the in-vivo device 840 and/or an erratically shaped tracking curve. According to embodiments of the present invention, the path between the splenic flexure '3' and the rectum '4' may be modeled as a third straight line extending from the second straight line as may be shown in FIG. 4B as the line between point '3' and point '4'. Methods of modeling the path between the splenic flexure '3' and the rectum '4' may be similar to methods described for modeling the path between the ceacum '1' and the hepatic flexure '2'. Other suitable method may be used.

According to one embodiment of the present invention, the rate of advancement along the model based path may be proportional to rate of advancement along the raw tracking curve. For example, in a case where the in-vivo imaging device 840 has advanced half way along the path between the detected ceacum, point '1', and the hepatic flexure, point '2', on the raw tracking curve (FIG. 4A), the in-vivo imaging device 840 may be shown to have advanced half way along the model based path (FIG. 4B) between point '1' and point '2'. This may be analogous to straightening out the raw tracking curve, e.g. straightening the raw tracking curve between the ceacum '1' and the hepatic flexure '2' and possibly scaling it.

In one embodiment of the present invention, when modeling the advancement of the in-vivo imaging device 840, the contribution of the secondary motion in the model based curve may be de-emphasized and the contribution of the primary motion may be emphasized, for example by weighting, to better represent the progression of the in-vivo device 840 along the colon. For example, while modeling the path of the in-vivo device 840, secondary motions such as tumbling, jittering, changing orientation may be disregarded and/or their contribution to the modeled advancement of the in-vivo device may be reduced and/or diminished.

Figure 5:
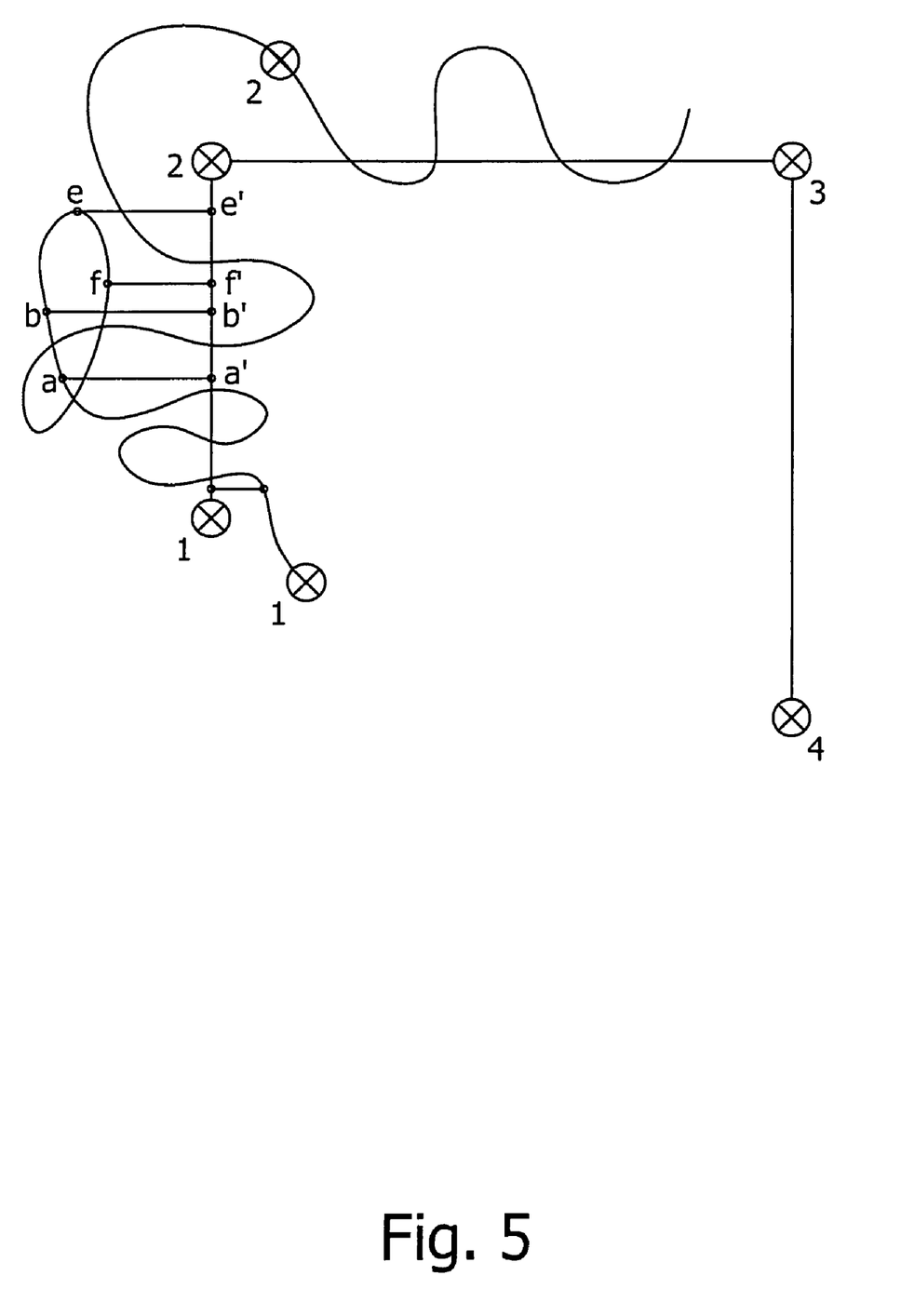
FIG. 5 is a schematic example of a method for projecting raw tracking data points onto a model based curve according to an embodiment of the present invention.

Reference is now made to FIG. 5 showing a schematic example of a method for projecting raw tracking data points and/or a portion of the raw tracking data points onto a model based curve. For example, the ceacum (milestone data point 1) and the hepatic flexure (milestone data point 2) may be identified on the raw tracking curve as may be described herein. Data points, e.g. data points (a, b, e, f) along the raw tracking curve may then be projected onto points (a', b', e', f') along the model based curve. In some examples, projection may reduce the contribution of secondary motion while providing a good indication the relative position of the in-vivo device 840 between the identified milestone data points. In one example, back and forth motion between milestones may be identified. For example although on the raw tracking curve point (e) preceeds point (f), on the model based tracking curve corresponding point (f') is projected to a point on the model based tracking curve that is below projected point (e'). In this example, the projection method indicates that between the projected points (e') and (f') the in-vivo device 840 receded for a distance. Other methods of projection may be used to translate motion along the raw tracking curve to motion along the model based curve.

One or more methods may be used to differentiate between primary and secondary motion. For example, corresponding image data may be inspected to detect periods when the in-vivo device 840 is stagnating and to reduce the contribution of the raw tracking curve data during that period. Alternately corresponding image data may be inspected to detect periods when the in-vivo device 840 is progressing and increase the relative contribution of the raw tracking curve data during that period. In other examples, data collected in-vivo other than image data may be inspected to help differentiate between primary and secondary motion. In addition, other methods of inspecting and/or processing image data to determine advancement of the in-vivo device 840 may be implemented in modeling the advancement of the in-vivo device 840 through the colon.

According to other embodiments of the present invention, the model based tracking curve may only indicate to the user, e.g. the physician, the section of the colon from which the in-vivo device is capturing data and/or the section of the colon in which the in-vivo device may be positioned at a given moment in time. For example a model colon may be displayed along side a streaming display of the image frames captured by the in-vivo device 840 and the relevant section of the displayed model colon may be highlighted.

According to some examples, the in-vivo device may temporarily move backwards or regress through parts of the colon and the model based tracking curve may give indication of regression as well as advancement.

Figure 6:
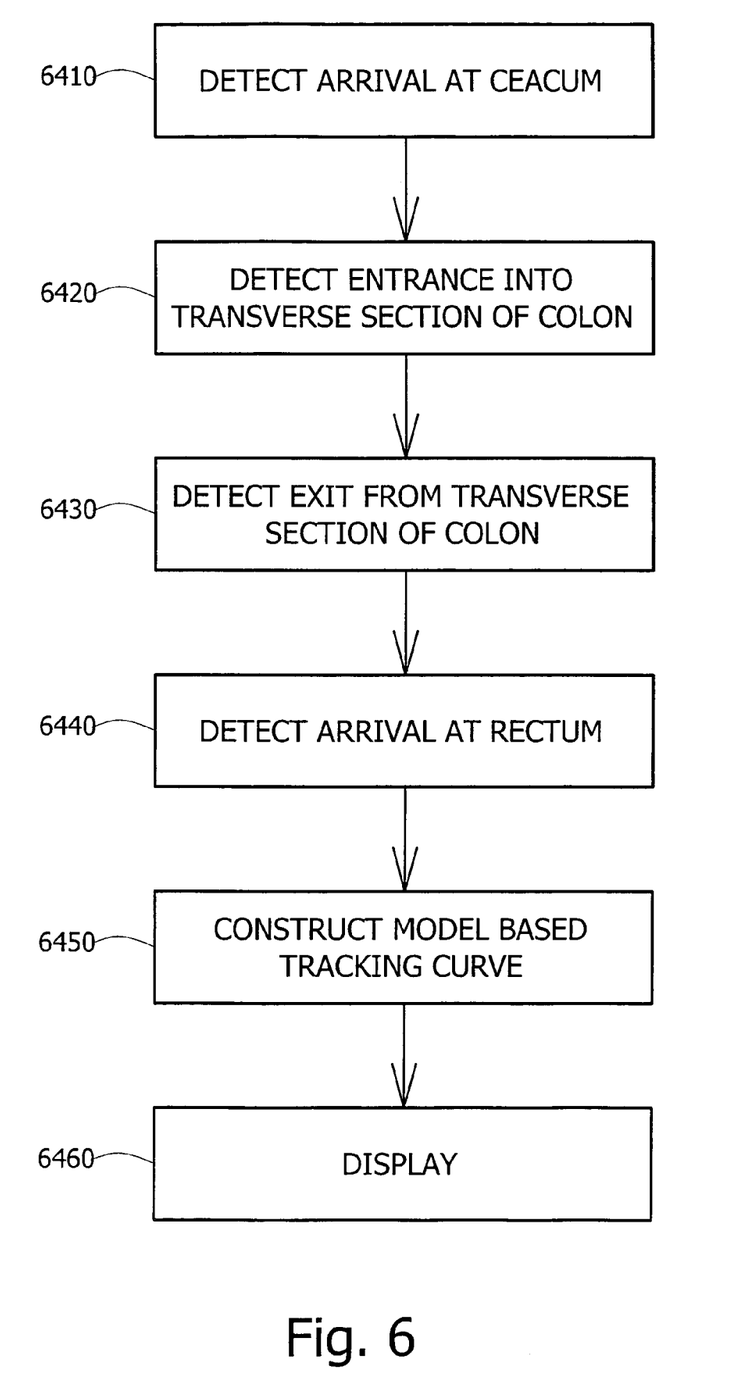
FIG. 6 is a flow chart describing a method for modeling a tracking data curve of an in-vivo device passing through a colon in accordance with some embodiments of the invention.

Reference is now made to FIG. 6 describing a method for model base tracking of an in-vivo device 840 passing through a colon in accordance with some embodiments of the invention. In block 6410, detection of the arrival of the in-vivo device 840 into the ceacum may be determined. According to one embodiment of the present invention, the user may be prompted to indicate a point along the image stream at which the in-vivo device 840 may have reached the ceacum. In another example automatic detection of the ceacum based on data analysis may be implemented. According to one embodiment, automatic detection may be based on image data captured. For example, a change and/or a specified change in color of the image data captured may indicate arrival to the ceacum. In another example, the lumen wall structure of the ceacum may be identifiably different than the lumen wall structure of the small intestine, e.g. lack of villi in the ceacum. For example, identification of blood vessels, e.g. artery and/or vein like structures on the wall of the lumen may be used to detect entrance into the ceacum. Detection may be based on the typical structure of the ceacum as compared to the small intestine. For example, the ceacum may typically be a relatively voluminous lumen as compared to the small intestine and detection may be based on of the change in volume of the lumen. Another example, automatic image analysis may be performed to detect tissue folds that may be typically to the ceacum as compared to the small intestine. In other example, a location just before the ceacum may be identified, e.g. identification of the terminal ileum. In some example, the in-vivo device may typically reside in the terminal ileum with typically back and forth motion prior to passing through the ileocecal valve to enter the ceacum. Other methods may be used.

In other examples, raw tracking curve data may be used to determine arrival at the ceacum. Typically, the ceacum is a sac-like and/or pouch structure such that the in-vivo device 840 may dwell within it for a period of time until a contraction and or a fluid flow may thrust the in-vivo device 840 along the colon. For example, a first period where the capsule is determined to dwell in the same location for at least a given amount of time may indicate that the in-vivo device is within the ceacum and/or terminal ileum. In another example, the in-vivo device may have a tendency to vibrate and/or jiggle within the ceacum, detection of the vibration motion typical to the ceacum may be an indication that the in-vivo device is within the ceacum. Vibration and/or jitter movement may be detected from the raw tracking curve or from inspection of other data, e.g. image data, or other data. Jiggling may be due to free motion of the in-vivo device within the pouch structure of the ceacum while for example, the patient is moving. In another example, the ceacum may be identified as the point along the tracking curve at the lowest right hand corner prior to an ascending motion. Other methods and/or a combination of methods may be used to determine when and/or at what point in relation to the data captured, the in-vivo device 840 may be located in the ceacum. The point in time or the corresponding data point of captured data determined and/or estimated may be marked by the user and/or by the automated process. In some examples, the detection of the ceacum may be a semi-automated process. In other examples, detection of the ceacum may be performed in real time.

In block 6420 and 6430 detection of entrance and exist through the transverse colon may be performed. This detection may be manual, e.g. user determined, may be automated, e.g. detected with colon section detector unit 888 and/or may be semi-automated, e.g. user assisted detection.

According to one embodiment of the present invention, the detection of the entrance and exit through the transverse colon may be semi-automated, e.g. detected based on user assistance. In some examples a point on the raw tracking curve and/or an image frame captured along the transverse colon may be detected by the colon section detector unit 888 and the user may be asked to scroll back and forth from the identified image frame to identify the entrance and exit areas of the transverse colon.

Automatic detection of a point along the transverse colon may be based on inspection of the raw tracking curve. For example, typically, the raw tracking curve through the transverse colon may be smoother as compared to raw tracking curve through other sections of the colon. This may be due to the relatively fast speed at which the in-vivo device travels through the transverse section of the colon. As such the colon section detector unit 888 may identify a point along the transverse colon by identifying the smoothest curve (e.g. 422 in FIG. 4A) and/or longest line along the tracking curve. An image frame captured at a time period corresponding to a point on this line may have been captured within the transverse section of the colon. In another example, the first segment of the raw tracking curve to pass the mid-line axis (240) of the body may typically correspond to a period in which the in-vivo device 840 may be in the transverse colon. In one example, the colon section detector unit 888 or other processing unit may identify a section of the tracking curve that crosses a mid-line axis of the body and define that section as a section of the tracking curve when the in-vivo device resided or traveled through the transverse section of the colon. The transverse colon is typically the section of the colon that transports the in-vivo device 840 across and/or past the mid-line axis of the body. Identification of the image frame along the transverse colon may be based on detection of an image frame captured along the longest and/or smoothest line in the raw tracking curve. Other suitable features of the raw tracking curve may be analyzed to automatically detect an image frame captured within the transverse section of the colon.

In another embodiment of the present invention, RSSI measurements from the RSSI unit 804, may be used to detect data captured along the transverse section of the colon. For example, the signal strength of a received signal, e.g. signal caring image data, may be determined. The received signals may correspond to data points on the raw tracking curve. Milestone data points may be identified based on the signal strengths of the received signals. Typically the transverse section of the colon lies close to the surface of the abdominal wall as compared to the ascending and descending section of the colon and often the highest RSSI values are recorded during the period in which the in-vivo device 840 may be present within the transverse section of the colon. In one example, the colon section detector unit 888 may detect RSSI values to determine a point along the transverse section of the colon and/or to depict an image frame that was captured in the transverse section of the colon.

Other suitable methods may be used to automatically detect a point within the transverse section of the colon and/or other sections of the colon. For example, image analysis and/or motility analysis may be used to detect an image frame that was captured in the transverse section of the colon. A combination of methods may be used to automatically detect a point and/or an image frame in the transverse section of the colon.

In one example, inspection and/or detection of the imaged lumen shape may be used to automatically detect a point within the transverse section of the colon. For example, the typical triangular shaped lumen may be detected by automatic methods and may be indicative that the in-vivo device is present within the transverse section of the colon. In other examples, detection of organs outside the lumen that may be seen through the lumen wall, e.g. liver may be used to identify, for example, the location of the hepatic flexure.

In other examples, inspection of the movement pattern of the in-vivo device 840 may be used to determine at least one milestone data point. For example, speed of travel may be used to identify a period at which the in-vivo device 840 may be passing through the transverse section of the colon. For example a period at which the in-vivo device 840 reaches a peak velocity may be identified as a period at which the in-vivo device 840 is traveling through the transverse section of the colon. In another example, a speed above a defined threshold may indicate the in-vivo device 840 is traveling through the transverse section of the colon. In other examples, acceleration of the in-vivo device may be inspected and peaks in the acceleration may be used to identify the flexure points where the largest change in speed may be expected to occur.

Subsequent to automatic detection of an image frame captured within the transverse section of the colon, a user may be asked to inspect image frames before and after the detected image to identify and mark the hepatic flexure and to the splenic flexure.

In other embodiments of the present invention, identification of the entrance and exit through the transverse section of the colon may be fully automated and detected by the colon section detector unit 888. For example, RSSI measurements may be used to detect the span of the transverse section of the colon, e.g. from the entrance to the exit of the transverse section of the colon, for example, without user assistance. In other examples, feature analysis of the raw tracking curve, motility analysis, image analysis, and or other suitable analysis may be used to automatically detect data captured along the transverse section of the colon. Typically, a combination of methods may be used.

In block 6440, the arrival and/or exit of the in-vivo device through the rectum may be detected. Detection of the excretion of the in-vivo device may be performed by image analysis, for example, it may be clear from inspection of the image captured that the in-vivo device is not within the body lumen, or by temperature measurement, reduction in temperature may indicate that the in-vivo device existed the body. In other examples, data collection may end, e.g. the image stream may end, before excretion and the arrival to the rectum may not be required.

In block 6450, a model based tracking curve may be constructed based on the detected milestones, e.g. ceacum, hepatic flexure, splenic flexure, rectum or exist from body. According to other embodiments of the present invention, the model based tracking curve may only indicate to the user, e.g. the physician, the section of the colon from which the in-vivo device is capturing data and/or the section of the colon in which the in-vivo device may be positioned at a given moment in time. For example a model colon may be displayed along side a streaming display of the image frames captured by the in-vivo device 840 and the relevant section of the displayed model colon may be highlighted.

In another embodiment, the model based tracking curve may be a marker following synthesized path between milestones detected as may be described herein. The rate of advancement through this synthesize path may be determined based on the raw tracking data information, based on the image scenery, based on motility measurements or based on other factors.

The results of the model based tracking curve may be displayed for example, displayed together with the display of the in-vivo captured data. For example, the advancement of the in-vivo device may be shown by a moving marker along a synthesized path while streaming the image stream captured such that the position along the synthesized path of the marker may correspond to the concurrent image frame displayed (block 6460). Other methods and steps may be implemented.

According to some embodiments of the present invention, a modeled distance and/or path length may be determined. For example, an approximate distance that in-vivo device 840 is to travel between for example the ceacum and the rectum or between defined locations of the colon may be estimated and/or determined from the modeled based tracking curve. In some examples, the path length along specific sections of the colon may be calculated. The estimated path length may be determined based on the modeled tracking curve or based on other and/or more information.

Figure 7:
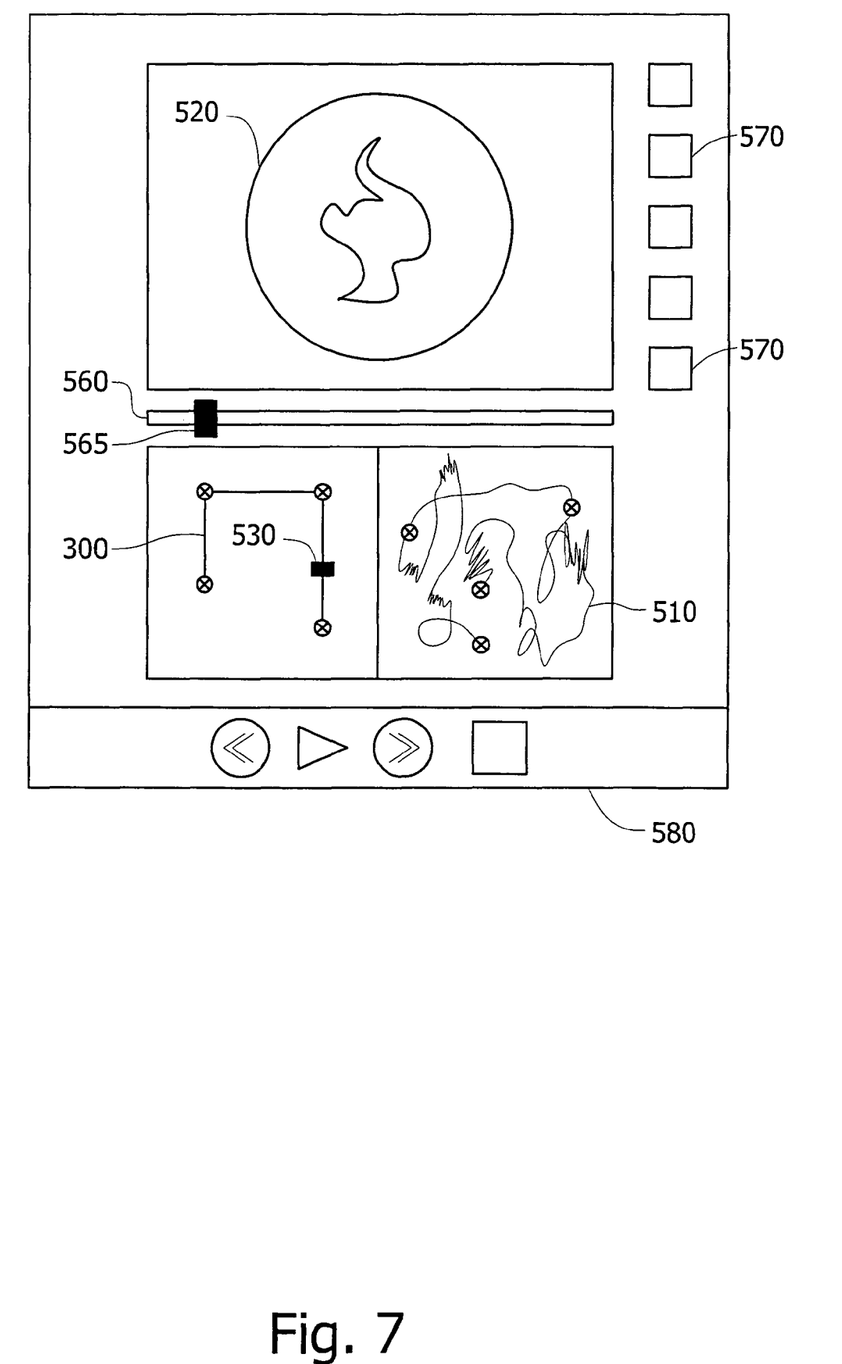
FIG. 7 is a sample graphical user interface (GUI) according to an embodiment of the present invention.

Reference is now made to FIG. 7 showing a sample graphical user interface (GUI) according to embodiments of the present invention. According to embodiments of the present invention a graphical presentation of the modeled tracking curve may be displayed. For example, a streaming display of image frames captured by the in-vivo device may be displayed along side a display of a moving marker along the modeled path to indicate a modeled location of the in-vivo device corresponding to a currently displayed image frame from the streaming display of the image frames. According to embodiments of the present invention, an image stream captured within a body lumen, e.g. within the colon, may be displayed in area 520, e.g. as a streaming display. A sliding marker 565 may slide along time bar 560, a color bar, a change in scenery bar or other bar as the image frame displayed for example, advances from the beginning of the image stream toward the end. Control buttons 580 may be used to play and/or display the stream of image frames forwards, backwards and at different speeds. In addition, a location marker 530 may slide along a model based tracking curve 300 to indicate the position of the in-vivo device 840 corresponding to the current image frame displayed in 520. Along side the model based tracking curve 300, the raw tracking curve 510 may additional be displayed showing raw tracking data based on position sensor data. In some examples the GUI display may allow the user to save thumbnails of selected image frames for reference. For example, the user when prompted may indicate image frames captured near and/or at the ceacum, hepatic flexure, splenic flexure, rectum, and at other suitable milestones of the colon. In other examples the user may save thumbnails of points of interest for diagnostic purposes.

According to one example, the user may initially quickly view sections of the image stream to identify milestones to initiate construction of the model based tracking curve 300. Subsequently, the user may view the image stream for diagnostic purposes. In other examples, identification of the milestones to initiate construction of the model based tracking curve 300 and diagnostic review may occur simultaneously. In yet other examples, construction of the model based tracking curve may occur automatically prior to the user review. In yet other examples, the construction of the model based tracking curve may occur automatically prior to the user review and the user may later modify the model based tracking curve, for example, by identifying new milestones, e.g. points in the tracking curve corresponding to the ceacum, hepatic flexure, splenic flexure, and rectum.

Although specific details may be described for constructing a model based tracking curve to track the advancement of an in-vivo device 840 through a colon, a similar system and method may be used to construct a model based tracking curve to track the advancement of the in-vivo device 840 through the entire GI tract and/or through other parts of the GI tract.

While certain features of the invention have been illustrated and described herein, many modifications, substitutions, changes, and equivalents will now occur to those skilled in the art. It is, therefore, to be understood that the appended claims are intended to cover all such modifications and changes as fall within the true spirit of the invention.

What is claimed is:

1. A system for modeling a raw tracking curve of an in-vivo device passing through a colon, the system comprising:
    a data recorder unit to receive and store a plurality of in vivo signals sent from the in-vivo device passing through the colon;
    a processor to construct the raw tracking curve based on the strength of the received signals, said raw tracking curve representing estimated location of the in-vivo device;
    a colon section detector unit configured to identify milestone data on the raw tracking curve corresponding to defined locations in the colon and to translate the raw tracking curve to a modeled curve; and
    a monitor configured to display a graphical presentation of the modeled tracking curve.

2. The system according to claim 1 comprising an RSSI unit to determine signal strength of data of the raw tracking curve.

3. The system according to claim 1 comprising:
    a receiver to receive image data captured in-vivo, wherein the colon section detector unit is configured to analyze the image data received.

4. The system according to claim 1 wherein the defined locations in the colon include at least a flexure point.

5. The system according to claim 1 wherein the defined locations in the colon include at least a ceacum.

6. The system according to claim 1 wherein the defined locations in the colon include at least a transverse section of the colon.

7. The system according to claim 1 comprising a user input device configured to receive user input to identify the milestone data.

8. The system according to claim 1 wherein the colon section detector unit is configured to identify a section of the raw tracking curve that passes a mid-line axis of a body.

9. The system according to claim 1 wherein the colon section detector unit is configured to analyze a movement pattern of the in-vivo device.

10. The system according to claim 1 wherein the colon section detector unit is configured to project at least a portion of the raw tracking curve onto the modeled curve.

11. The system according to claim 1 wherein said monitor is further configured to display a streaming display of image frames captured by the in-vivo device and a moving marker along the modeled curve to indicate a modeled location of the in-vivo device corresponding to a displayed image frame from the streaming display of the image frames.

12. The system according to claim 1 wherein the modeled curve has a pre-determined shape.

* * * * *